(12) United States Patent
Sheu (10) Patent No.: US 6,503,542 B2
(45) Date of Patent: Jan. 7, 2003

(54) HERBAL COMPOSITIONS FOR TREATING IMMUNOLOGICAL DISORDERS

(75) Inventor: Shuenn-Jyi Sheu, Taipei (TW)

(73) Assignee: GloboAsia, L.L.C., Hanover, MD (US)

( * ) Notice: Subject to any disclaimer, the term of this patent is extended or adjusted under 35 U.S.C. 154(b) by 0 days.

(21) Appl. No.: 09/949,610

(22) Filed: Sep. 12, 2001

(65) Prior Publication Data

US 2002/0122833 A1 Sep. 5, 2002

Related U.S. Application Data

(63) Continuation-in-part of application No. 09/735,536, filed on Dec. 14, 2000.

(51) Int. Cl.[7] .......................... A01N 65/00; A61K 35/78
(52) U.S. Cl. .................. 424/728; 424/725; 424/757; 424/764; 424/773; 424/774
(58) Field of Search ................................ 424/728, 725, 424/757, 764, 773, 774

(56) References Cited

U.S. PATENT DOCUMENTS

| 5,281,583 A | 1/1994 | Soma et al. |
| 6,200,570 B1 | 3/2001 | Diwant et al. |
| 6,383,525 B1 * | 5/2002 | Sheu .......................... 424/728 |

* cited by examiner

Primary Examiner—Herbert J. Lilling
(74) Attorney, Agent, or Firm—Fei-Fei Chao; Venable, Baetjer, Howard & Civiletti, LLP (57) ABSTRACT

The present invention provides a pharmaceutical composition which comprises water extracts of *Tuber ophiopogon, Tuber pinelliae, Radix glycyrrhizae,* and *Radix pancis quinquefoli,* and 50% alcohol extraction of *Herba tridacis procumbentis.* The pharmaceutical compositions are especially effective in treating patients with immunological disorders, such as asthma, atopic eczema, atopic dermatitis, allergic rhinitis and rheumatoid arthritis.

25 Claims, 7 Drawing Sheets

HERBAL COMPOSITIONS FOR TREATING IMMUNOLOGICAL DISORDERS

RELATED APPLICATION

This application is a continuation-in-part of U.S. application Ser. No. 09/735,536 filed on Dec. 14, 2000, which is herein incorporated by reference.

FIELD OF THE INVENTION

The present invention relates to a novel medicinal herbal composition and its use for treating patients with immunological disorders, particularly IgE mediated diseases, which include, but are not limited to, allergic rhinitis, allergic conjunctivitis, allergic asthma, atopic eczema, atopic dermatitis, food allergy, hyper IgE syndrome, and rheumatoid arthritis. The novel medicinal herbal composition contains aqueous extracts of *Tuber ophiopogon, Tuber pinelliae, Radix glycyrrhizae, Herba tridacis procumbentis,* and *Radix pancis quinquefolii.* The present invention also relates to a method for making the medicinal herbal composition and methods for treating patients with the medicinal herbal composition.

BACKGROUND OF THE INVENTION

Antigen-induced, particularly allergen-induced immunological disorders, such as asthma, has long been known as one of the serious health problems in the world. Allergy in one form or another afflicts more than 20% of the world population. In recent years, statistics shows that the onset of the allergic-related immunological disorders has shifted to the younger population, which means that more children and/or adolescents have developed symptoms of allergen-induced immunological disorders. For instance, in Taiwan, the prevalence of childhood asthma increased from 1.3% in 1974, to 5.07% in 1985, and to 5.8% in 1991. Also, allergic rhinitis increased from 7.84% in 1985 to 20.67% in 1991. Furthermore, atopic eczema was 1.43% in 1974 and 1.23% in 1985, in 1991, it was 3.84%. It is believed that the early onset of allergen-related immunological disorders are likely due to environmental pollution.

Respiratory allergies are immunoglobulin E (IgE)-mediated immune response. (See Brinker, *J. Naturopathic Medicine*, (1993):4:64–68). There are two major types of respiratory allergic reactions: The immediate hypersensitivity reactions include allergic rhinitis (hay fever) and allergic (extrinsic) bronchial asthma. Allergic rhinitis is brought on by antigen/IgE binding to sensitized mast cells and basophils, causing a decrease in cAMP which leads to release of esosinophil chemotactic factor and histamine. Histamine binding to H1-receptors has several results. It increases vasodilation, capillary permeability, and smooth muscle contraction, manifesting as nasal congestion with watery discharge, sneezing, and itching eyes.

Allergic asthma is another IgE-mediated immune response in which mast cells release histamine, bradykinin, and arachidonic acid metabolites including the leukotriene slow reacting substances of anaphylaxis and thromboxane/prostaglandin bronchoconstrictors. Platelet activating factor is another potent asthma mediator released from a number of leukocytes. In this condition, histamine, which released after a decrease in cAMP, acts on H1-receptors to cause bronchospasm. It is also responsible for bronchoconstriction due to cholinergic reflex action and half of the prostaglandin generation in anaphylaxis.

While the percentage of affected population and severity of the diseases are rising, current methods for treating allergy still primarily depend on empirical and serendipitous findings rather than from scientific approach. At present, most patients are treated with drugs that aim at controlling symptoms resulted from the release of mediators by effector cells. Although some drugs appear to be effective in short term and with few occurrences of adverse effects, long term effects for preventing disease progression and permanent destruction are still largely unknown. For example, long-term oral therapy, such as steroid therapy, for treating asthma, is now known to be associated with multiple debilitating effects such as growth delay, osteoporosis, and adrenal suppression.

Traditional Chinese herbs and medicinal combinations have been known for improving function of immune system and treating various chronicle immunological disorders. For example, Hamasaki et al., *J. Ethnopharmacology*, (1997) 56:123–131, disclose a Chinese herbal medicine, Shinpi-To, which inhibits IgE-mediated leukotriene synthesis in rat basophilic leukemia-2H3 cells. Shinpi-To is a freeze-dried granular Chinese herbal medicine prepared from extract of seven (7) medicinal herbs, i.e., Ephedrae herba (*Ephedra sinica* Stapf), Armeniacae semen (*Prunus armeniaca* Linne), Magnoliae cortex (*Magnolia obovata* Thunberg), Aurantii nobilis Pericarpium (*Citrus unshiu* Markovich), Glycyrrhizae radix (*Glycyrrhiza uvalensis* Fischer), Bupleuri radix (*Bupleurum falcatum* L.), and Perillae herba (*Perilla frutescens* Britton var. acuta Kudo). Shinpi-To is useful for treating childhood asthma.

Toda et al., *J. Ethnopharinacology*, (1988) 24:303–309, discloses a Chinese herbal medicine, Saiboku-To, which shows inhibitory effects on histamine release from mouse peritoneal mast cells. Saiboku-To is useful for treatment of asthma. Saiboku-To contains ten medicinal herbs: *Bupleurum falcatum* L., *Pinellia ternata* Breitenbach, *Poria cocos* Wolf, *Scutellaria baicalensis* Georgi, *Zizyphus vulgaris* Lam., *Panax ginseng* C. A. Meyer, *Magnolia oborata* Thumberg, *Glycyrrhiza glabra* L., *Perilllae frutescens* Britton var. acuta Kudo, and *Zingiber officinale* Roscoe.

Li et al., *Immunopharmacology*, (1999), 43:11–21, discloses a Chinese herbal medicine, Hochu-Ekki-To, which shows effects on restoring stress-induced immunosuppression. Hochu-Ekki-To consists often (10) ingredients, i.e., Ginseng Rx., Atractylodis alba Rz., Astragali Rx., *Angelicae sinensis* Rx., Jujubae Fr., *Citri reticulatae* Pc., Bupleuri Rx., Glycyrrhizae Rx. Preparata, *Zingiberis recens* Rz., and Cimicifugae Rz.

Zou et al., *Chinese Traditional and Western Medical Magazine*, (1996):529–532, discloses a Chinese herbal medicine, Wenyang Tongluo mixture, for treating cold-type asthma patients. It shows effects on improving pulmonary ventilation functions, regulating adrenergic β-receptors of peripheral blood lymphocytes, and decreasing the serum level of 5-hydroxytryptamine. Wenyang Tongluo mixture contains twelve (12) medicinal herbs, i.e., Red Ginseng, Zhi Fu Pian, Yin Yang Huo, Dried Ginger (*Zingiberis recens* Rz.), Zhi Huang Zhi, *Angelicae sinesis* Rx., Ephedra, Polygalae Rx., Sang Baipi, Sheng Shi Gao, Schisandrae Fr., and Licorice (Glycyrrhizae Rx. Preparata).

There is also an ophiopogon decoction disclosed on the internet (www.herb.com.tw) which shows a combination of six (6) herbs, i.e., Ophiopogonis Rx., Pinelliae Rz. Preparata, Oryzae Sm., Jujubae Fr., Ginseng Rx., and Glycyrrhizae Rx. It is useful for treating bronchitis and bronchial asthma.

In dealing with Chinese herbal medicine, it is critical to control the quality of the herbs, because the contents and/or active ingredients of the herbs can vary significantly due to herb's growing conditions and harvesting seasons/techniques. If any of the critical conditions and factors, such as the locality where the herbs are grown, the season(s) when the herbs can be harvested, and the manufacturing process of the herb, are not met, the effectiveness of the herbal medicine would vary. So far, there has been no report showing the adoption of any reliable scientific method for monitoring the quality of the Chinese herbal medicine.

The present invention provides novel and non-toxic pharmaceutical compositions derived from herbs, which are primarily found in China and Taiwan. The combined use of these herbs has never been found in any literatures or reports. These pharmaceutical compositions are particularly effective in treating patients with immunological disorders, especially IgE mediated diseases. The pharmaceutical compositions of the present invention have demonstrated special effects on down-regulation of the synthesis of interleukin 4 (IL-4) and suppression of IgE. In addition, to effectively control the quality of the herbs, the present invention fingerprints each herb using thin layer chromatography (TLC) and high performance liquid chromatography (HPLC) to ensure that each herb used in the composition contains consistent and reproducible ingredients.

SUMMARY OF THE INVENTION

The present invention provides a pharmaceutical composition which is effective in treating patients with immunological disorders, including, but not limited to, allergic rhinitis, allergic conjunctivitis, allergic asthma, atopic eczema, atopic dermatitis, food allergy, hyper IgE syndrome, and rheumatoid arthritis.

The pharmaceutical composition contains aqueous extracts of *Tuber ophiopogonis* (ophiopogon), *Tuber pinelliae* (pinellia), *Radix glycyrrhizae* (raw licorice), *Radix pancis quinquefolii* (American ginseng) and *Herba tridacis procumbentis* (lantern tridax). Ophiopogon, pinellia, raw licorice, and American ginseng are preferably extracted in water. Lantern tridax is preferrably extracted in alcohol, more preferably in 50% alcohol. The preferred weight ratio of ophiopogon, pinellia, raw licorice, American ginseng and lantern tridax is about 3:2:1:1:1.

Each of the aqueous extracts of ophiopogon, pinelliae, raw licorice, American ginseng and lantern tridax is preferably separately filtered and condensed. The solid content of the condensate of ophiopogon constitutes about 20–30% by weight, preferably about 25% by weight, of the ophiopogon raw material. The solid content of the condensate is the condensate excluding the water. In the case of ophiopogon, the condensate contains substantial amount of water (i.e., about 58% of the condensate of ophiopogon is water). The solid contents of the rest of the herbs are about the same as the condensate (i.e., the water content was insignificant). The condensate of pinellia constitutes about 15–25% by weight, preferably about 20% by weight, of the pinellia raw material. The condensate of raw licorice constitutes about 15–25% by weight, preferably about 20% by weight, of the raw licorice raw material. The condensate of American ginseng constitutes about 19–29% by weight, preferrably about 24.3% by weight, of American ginseng raw material. The condensate of lantern tridax constitutes about 5–10% by weight, preferably about 7.8% by weight, of lantern tridax raw material.

Except for ophiopogon which is not granulated, each of the condensates of pinellia, raw licorice, American ginseng, and lantern tridax are individually granulated to form individual granules. Before granulation, an excipient, preferably corn starch, is added to the condensate to confer a suitable form of the granules. The individual granules and the condensate of ophiopogon are then mixed together to form mixed granules, which are then encapsulated.

The granules of pinellia constitute about 20–30% by weight, preferably about 25% by weight, of the pinellia raw material. The granules of raw licorice constitute about 16–26% by weight, preferably about 21% by weight, of the raw licorice material. The granules of American ginseng constitute about 27–37% by weight, preferably about 32% by weight, of the American ginseng raw material. The granules of lantern tridax constitute about 37–47% by weight, preferably 42% by weight, of the lantern tridax raw material.

The present invention also provides a method of making the pharmaceutical composition. The method requires an extraction of ophiopogon, pinellia, raw licorice, American ginseng and lantern tridax individually. Ophiopogon, pinellia, raw licorice, and American ginseng are extracted in water by decocting. Lantern tridax is extracted in alcohol, preferably 50% alcohol, by refluxing. After the extraction, each individual extract is filtered to remove the remaining herb. The fitrate is then condensed by decompressed condensation at a temperature of about 55° C. and a vacuum of about 30 torr to form a condensate. An adequate amount of an excipient, preferably corn starch, is added to each of the condensate, except ophiopogon, to form an extraction paste, which is subject to granulation by spray-drying at an inlet temperature of about 105° C. and an outlet temperature of about 76–77° C. The respectively granules from pinellia, raw licorice, American ginseng, and lantern tridax are mixed with the condensate of ophiopogon to form the mixed granules, which can be encapsulated.

In addition, the ratio of aqueous extractant (by volume) to herb (by weight) is about 20:1. For water extraction, the preferable decocting time is about 30 minutes. The preferred alcohol extraction time is also about 30 minutes.

The pharmaceutical composition of the present invention, although containing the same five herbal mixture as in the parent application, differs from the parent composition in that the composition of the present invention contains aqueous extracts from the herbs, while the parent composition contains primarily powders of the herbs (except ophiopogon, which is also from the aqueous extract). The present pharmaceutical composition demonstrates better effects in terms of drug efficacy and efficiency than the parent composition, possibly due to the release of active ingredients from the extraction procedures.

BRIEF DESCRIPTION OF THE DRAWINGS

FIG. 1 shows an HPLC chromatogram of ophiopogon. Its entire chromatographic profile was detected at 214 nm wavelength using method 1 of the HPLC analysis (see infra). There were two discrete peaks, 6115-1 and 6115-2, which had a retention time of 11.5 min and 13 min, respectively, shown in the chromatogram. These two peaks could be used to identify ophiopogon.

FIG. 2 shows an HPLC chromatogram of pinellia. Two chemical markers, adenine and guanosine, were detected at 260 nm wavelength using method 2 of the HPLC analysis. Adenine has a retention time of 14.8 min. Guanosine has a retention time of 17 min.

FIG. 3 shows an HPLC chromatogram of raw licorice. A chemical marker, glycyrrhizin (Gly), was detected at 250 nm wavelength using method 1 of the HPLC analysis. Gly has a retention time of 46.4 min.

FIG. 5 shows an HPLC chromatogram of lantern tridax. There were four (4) distinctive peaks, FY-1 to FY-4, detected at 250 nm wavelength using method 2 of the HPLC analysis. FY-1 has a retention time of 28 min. FY-2 has a retention time of 31.6 min. FY-3 has a retention time of 33.5 min. FY-4 has a retention time of 18.3 min.

FIG. 8 is a comparative study of the effects of STA-36, STA-4, and control (the placebo group) on IgG and IgE in serum of female BALB/c mice. STA-36 is the pharmaceutical composition introduced in the parent case; STA-4 is the pharmaceutical composition of the present invention. * indicates significant difference (p<0.05) between STA-4 and control. Values are means±SEM. The dosage amount of STA-36 (20 mg/20 g mouse) was twice of the dosage amount (10 mg/20 g mouse) of STA-4 (i.e., STA-3:STA-4= 2:1). The results show that in terms of IgE, although both STA-36 and STA-4 show inhibition on IgE, only STA-4 is statistically significance from control. As of IgG, both STA-36 and STA-4 show increase in IgG. However, although it appears that STA-36 shows greater increase in IgG level than STA-4, neither increase is significantly different from the control.

FIG. 9 is a comparative study of the effects of STA-36 and STA-4 on Lung Functions. Values are means±SEM. Both STA-36 and STA-4 show significant improvement in lung functions (as determined by measurement of acetylcholine) as compared to control (P<0.05). Between the treatment of STA-36 and STA-4, although it appears that STA-4 had better effect than STA-36, the difference between STA-36 and STA-4 was nevertheless not statistically significant probably due to insufficient numbers of animals used in each group. The dosage amount of STA-36 (20 mg/20 g mouse) was twice of the dosage amount (10 mg/20 g mouse) of STA-4.

DETAILED DESCRIPTION OF THE INVENTION

In the parent application U.S. Ser. No. 09/735,536, six pharmaceutical compositions, each contains five (5) herbs, were introduced (so-called STA-3 series [STA-31 to STA-36]). The herbal contents of STA-31 to STA-36 are shown in Table 1.

TABLE 1

Herbal Compositions in the STA-3 Series

| Herbal Composition | Herb #1 | Herb #2 | Herb #3 | Herb #4 | Herb #5 |
|---|---|---|---|---|---|
| STA-31 | Tuber Ophiopogon | Tuber Pinelliae | Radix Glycyrrhizae | Radix Codonopsitis Pilosulae | Herba Adeno-stemmatis |
| STA-32 | Tuber Ophiopogon | Tuber Pinelliae | Radix Glycyrrhizae | Radix Codonopsitis Pilosulae | Herba Houttuyniae |
| STA-33 | Tuber Ophiopogon | Tuber Pinelliae | Radix Glycyrrhizae | Radix Codonopsitis Pilosulae | Herba Tridacis procumbentis |
| STA-34 | Tuber Ophiopogon | Tuber Pinelliae | Radix Glycyrrhizae | Radix Pancis Quinquefolii | Herba Adeno-stemmatis |
| STA-35 | Tuber Ophiopogon | Tuber Pinelliae | Radix Glycyrrhizae | Radix Pancis Quinquefolii | Herba Houttuyniae |
| STA-36 | Tuber Ophiopogon | Tuber Pinelliae | Radix Glycyrrhizae | Radix Pancis Quinquefolii | Herba Tridacis procumbentis |

Among the six STA-3 compositions, STA-36 is the most preferable one.

The present invention focuses on improving the therapeutic effect of STA-36 by applying various extraction methods to the herbs used in STA-36, namely *Tuber ophiopogonis* (ophiopogon), *Tuber pinelliae* (pinellia), *Radix glycyrrhizae* (raw licorice), *Radix pancis quinquefolii* (American ginseng), and *Herba tridacis procumbentis* (lantern tridax). The resulted pharmaceutical composition is called STA-4. Both STA-36 and STA-4 possess pharmaceutical effects on treating immunological disorders, particularly on suppression of IgE production.

Antigen or allergen-mediated asthma is a respiratory disease primarily due to chronic inflammatory reaction. The inflammatory reaction is mediated by the release of inflammatory factors, such as platelet activation factor, histamine, prostaglandin, and leukotrien, from the cells. Inflammatory reaction stimulates antigenic response in T lymphocytes (T cells), particularly CD4+ cells. There are two types of CD4+ cells. Th1 type of CD4+ cells secrets cytokine (IFN-γ). Th2 type of CD4+ cells secrets interleukin-4 (IL-4). Most of the allergic asthma patients are Th2 type. The allergen stimulates the Th2 cells to produce excess IL-4, which in turn induces the production and secretion of IgE from B lymphocytes.

A comparison between the herbal contents in STA-36 and STA-4 is shown in Table 2.

TABLE 2

Herbal Contents in STA-36 and STA-4

|  | Tuber Ophiopogon | Tuber Pinelliae | Radix Glycyrrhizae | Radix Pancis Quinquefolii | Herba Tridacis procumbentis |
|---|---|---|---|---|---|
| STA-36 | water extract | raw powder | raw powder | raw powder | raw powder |
| STA-4 | water extract | water extract | water extract | water extract | 50% alcohol extract |

The pharmaceutical names, botanical names, common names, families, and major ingredients of each of the herbs used in STA-36 and STA-4 are shown in Table 3.

TABLE 3

Pharmaceutical/Botanical Names and Major Ingredients of the Herbs in STA-3 Pharmaceutical Composition

| Common Name of the Herb | Pharmaceutical Name | Botanical/ Zoological Name | Family | Major Ingredients |
|---|---|---|---|---|
| Ophiopogon (black leek) | Tuber Ophiopogonis Japonici | Ophiopogon japonicus Ker-Gawl. | Liliaceae | Ophiopogonin, Ruscogenin, β-Sitosterol, Stigmasterol |
| American Ginseng | Radix Panacis Quinquefolii | Panax quinquefolium L. | Araliaceae | saponins, panaquilon |
| Pinellia | Tuber Pinelliae, Rhizoma Pinellia Ternatae | Pinellia ternata (Thunb.) Breitenbach | Araceae | coniine, protoanemonin, homogentisic acid, nicotine, aspartic acid, glutamic acid, arginine, β-sitosterol, cholesterol |
| Radix Glycyrrhizae | Radix Glycyrrhizae Uralensis | Glycyrrhizae-uralensis Fisher or Glycyrrhiza glabra Linné. | Leguminosae | Azetidine-2-carboxylic acid, Aspartate, Homoserine, Diaminobutyric Acid, Digitalis Glycoside |
| Lantern Tridax | Herba Tridacis procumbentis | Tridax procumbens Linn. | Compositae | polysaccharide |

Ophiopogon (*Radix ophiopogonis*) belongs to the family of Liliaceae. The tuber (root) of Ophiopogon has medicinal effects. The best harvesting season for ophiopogon is in the summer. After harvested, the tuber of ophiopogon should be washed clean to get rid of unwanted dirt or rootlets, which was followed by drying under sun to preserve for later use. Ophiopogon tuber is the enlarged part of the root. Ophiopogon could be found in provinces such as Zhejiang, Sichuan, and Jiangsu, of China. The aqueous extract of ophiopogon was reported by Yu et al. (1991), *China Journal of Chinese Materia Medica*, 16:584–585, to enhance the clearance of iv charcoal particles in mice, and antagonize the leukopenia caused by clophosphamide.

American ginseng (*Radix panacis quinquefolii*) belongs to the family of Araliaceae. The medicinal effects of American ginseng is in the root. American ginseng can be found in northern United States and Canada. It has also been widely cultivated in France and northern China. The best harvest season for American ginseng is in autumn.

Pinellia (*Tuber pinelliae, Rhizoma pinellia ternatae*) belongs to the family of Araceae. The tuber (after the cork layer has been removed) of pinellia has medicinal effects. The plant grows in Sichuan, Hubei, Henan, Guizhou, and Anhui provinces of China. The normal harvest season of pinellia is between July and September. Pinellia can be found in Taichung Shien of Taiwan.

Raw licorice (*Radix glycyrrhizae uralensis*) belongs to the family of Leguminosae. The root and stolon, with (unpeeled) or without (peeled) the periderm, of *Radix glycyrrhizae* have medicinal effects. *Radix glycyrrhizae* contains not less that 2.5% of glycyrrhizic acid ($C_{42}H_{62}O_{16}$), calculated on the basis of dried material, which can be used as chemical marker for *Radix glycyrrhizae*. *Radix glycyrrhizae* can be found in inner Mongolia, Gansu, Xinjiang, and northeastern China. The best harvest seasons for *Radix glycyrrhizae* are either in spring or autumn. In Taiwan, *Radix glycyrrhizae* can be found in Taichung Shien. Licorice root has anti-inflammatory properties and can be used alone to help release symptoms of asthma. See H. W. Morningstar, *Sentient Times: Alternative for Personal and Community Transformation* (1998), 6:16–17. Licorice roots are also useful for treating bronchitis. See T. David, *Miracle Medicines of the Rainforest: A Doctor's Revolutionary Work With Cancer And AIDS Patients* (1997), pp. 66–79.

Lantern tridax (*Herba tridacis procumbentis*) belongs to the family of Compositae.

The medicinal effects of lantern tridax come from the dried whole plant. Lantern tridax can be found in Nantou Shien, Taichung Shien, and Yunlin Shien, and the city of Taichung of Taiwan. Lantern tridax has also been found in South America and in the United States. The plant, with the academic name as *Tridax procumbens* Linn. and the common name as coatbuttons in the United States, has been found in the states of Florida, Hawaii, Puerto Rico, and Virgin Islands, as shown in the Plant Distribution Map from the Plants Database, Natural Resources Conservation Service, U.S. Department of Agriculture http://plants.usda.gov/ plants/cgi bin/plant profile.cgi?symbol=TRPR5.

Diwan et al., *Indian Journal of Physiology & Pharmacology* (1983), 27: 32–36, disclose that the juice extracted from the leaves of lantern tridax has effects resembling dexamethasone on wound contraction and granulation, but significantly counteracts the effects of dexamethasone on tensile strength and epithelization. Gan et al., *China Medical College Annual Bulletin* (1977), 8: 526, disclose that leaves of lantern tridax is useful for diminishing inflammation, releasing symptoms of fever, and curing pneumonia and cough.

The STA-36 herbal composition and the STA-4 herbal composition are prepared as follows:

A. Preparation of the STA-36 Herbal Composition.

The STA-36 herbal composition was prepared by the following method:

(1) The roots of pinellia, raw licorice and American ginseng, and the entire plant of lantern tridax were cut, dehydrated, ground, and passed through a sieve (preferably 40–120 mesh) to produce herbal powders.

(2) The root of ophiopogon was cut into small pieces and immersed in water in a decocting container where the water volume was at least 10 cm above the top of ophiopogon. The submerged ophiopogon was heated at 97 to 103° C. for about sixty (60) minutes twice to produce an ophiopogon extract solution. Then, the ophiopogon extract solution was passed through a sieve (approximately 100 mesh). The filtrate was collected. The ophiopogon filtrate was then condensed at a temperature of 50 to 60° C. under vacuum condition with pressure between 400 and 650 mm-Hg to obtain a liquid condensate with a desirable concentration. It was preferred that the liquid condensate was about 1/14 of the ophiopogon filtrate.

(3) The liquid condensate of ophiopogon was mixed with the herbal powders of the rest of the herbs. The mixture was then transferred to the fluidized granulator and placed in a spraying tube made of filtered fabric. The granulator was set at 90 to 110° C. After pre-heating for about five (5) minutes, the mixture was sprayed at about 40 to 55 seconds per time for an appropriate amount of times and the spraying tube was patted at a frequency of once in every 10 seconds. After granulation, the granules were dried and then cooled off. The granules were passed through sieves and packaged in PE bags. The preferred water content of the granules was less than 6%. The granules can be further encapsulated in any of the conventional capsules, including, but not limited to, natural gelatin, pectin, casein, collagen, protein, modified starch, and polyvinyl pyrrolidone.

B. Preparation of the STA-4 Herbal Composition:

The STA-4 herbal composition was prepared by the following method:

I. For Lantern Tridax:

(1) The entire plant of lantern tridax was cut into small pieces.

(2) About 20 times (by volume) of 50% alcohol (v/v) (., extractant) was added to and mixed with about 1 time (by weight) of the small pieces of lantern tridax.

(3) The herb, together with its extractant, was heated by refluxing heat for about 30 minutes. This process produced an alcohol extract of lantern tridax.

(4) After the extract was cooled down, the alcohol extract of lantern tridax was filtered through a sieve (approximately 100 mesh). The filtrate was collected. The filtrate was then condensed by a decompressed condensation method at a temperature of 50 to 60° C. (preferably at 55° C.) under vacuum condition (at 30 torr) to obtain a condensate. Preferably, the solid content of the condensate is about 7.8% by weight of the raw material. The solid content of the condensate is the condensate excluding 50% alcohol. In the case of lantern tridax, the solid content of the condensate is about the same as the condensate (because very little amount of water is in the condensate).

(5) An adequate amount of corn starch (as excipient) was added to the condensate to produce an herbal paste.

(6) The herbal paste was dried by spray-drying method to form the lantern tridax granules (preferably about 42% by weight of the raw material).

II. For pinellia, raw licorice and American ginseng:

(1) The tuber of pinellia and the roots of licorice of American ginseng were separately cut into small pieces.

(2) For each herb, about 20 times (by volume) of water was added to and mixed with about 1 time (by weight) of the small pieces of the individual herb, respectively.

(3) Each herb, which was submerged in water, was heated by decocting for about 30 minutes, resulting in producing water extracts of ophiopogon, pinellia, raw licorice, and American ginseng respectively.

(4) After the respective extract was cooled down, each extract was separately filtered through a sieve (approximately 100 mesh). Each of the filtrate was collected, and then condensed by a decompressed condensation method at a temperature of 50 to 60° C. (preferably at 55° C.) under vacuum condition (at 30 torr) to obtain a liquid condensate for each of the herb. It is preferably that the solid content of the condensate of pinellia is about 20% of the pinellia raw material; the solid content of the condensate of raw licorice is about 20% of the raw licorice raw material; and the solid content of the condensate of American ginseng is about 24.3% of the American ginseng raw material. The solid content of the condensate of pinellia, raw licorice, or American ginseng is the condensate excluding the water.

(5) An adequate amount of corn starch (as excipient) was added to each of the condensate then granulated by spray-drying method to produce individual granules.

(6) The individual granules, together with the granules from lantern tridax, were mixed together to form mixed granules.

III. For Ophiopogon:

The tuber of ophiopogon was condensed in accordance with the procedures of II (1)–(4). The only difference between the condensate of ophiopogon and those of the pinellia, raw licorice, and American ginseng was that the ophiopogon condensate contained a significant amount of water while the rest of the condensates were almost deprived of water. For 9 g of ophiopogon raw material, the condensate was about 5.4 g in which about 2.25 g was solid content and 3.15 g was water.

The liquid condensate of ophiopogon was mixed with the rest of the herbal granules.

The gram weights of the herbs in the raw materials, STA-36, and STA-4 are illustrated in the following Table 3a:

|  | Ophiopogon | Pinellia | Raw Licorice | American ginseng | Lantern tridax | Total Weight (Oral Dosage Form) | Ratio (Dosage) of STA-36/STA-4 |
|---|---|---|---|---|---|---|---|
| Raw Material | 9 g | 6 g | 3 g | 3 g | 3 g | 24 g | |
| STA-36 | 5.4 g (2.25 SC* + 3.15 g water) | 6 g (herbal powders) | 3 g (herbal powders) | 3 g (herbal powders) | 3 g (herbal powders) | 20.4 (herbal powders) | 2 |
| STA-4 | 5.40 g | 1.50 g | 0.63 g | 0.96 g | 1.25 g | 10.20 g | 1 |

-continued

|  | Ophiopogon | Pinellia | Raw Licorice | American ginseng | Lantern tridax | Total Weight (Oral Dosage Form) | Ratio (Dosage) of STA-36/ STA-4 |
|---|---|---|---|---|---|---|---|
|  | condensate (2.25 g SC* + 3.15 g water) | granules (1.20 g SC* + 0.30 g Corn Starch) | granules (0.60 g SC* + 0.03 g Corn Starch) | granules (0.73 g SC* + 0.23 g Corn Starch) | granules (0.23 g SC* + 1.02 g Corn Starch) | (9.74 g of granules and ophiopogon condensate + 0.46 g of Corn Starch) |  |

*SC = Solid Content (which is the dried condensate [condensate excluding water or solvent]).

In Table 3a, the "raw material" line shows the weight of each herb before processing. The "STA-36" and "STA-4" lines show (1) what the final form of each of the herbs was; and (2) what the final weight of each of the herbs was. For example, in STA-36, except for ophiopogon which was in the form of condensate, pinellia, raw licorice, American ginseng, and lantern tridax were all in the form of herbal powders. Also, except for ophiopogon which contained less weight than its raw material, the herbal powders of the rest of the herbs in STA-36 maintained the same weight as their raw materials.

However, in STA-4, only ophiopogon maintained the same final form as that in STA-36, i.e., as condensate. The gram weight of the rest of the herbs, after gone through extraction, condensation, and granulation, had been substantially reduced, as indicated in Table 3a. In addition, to assist in stabilizing the condensate during granulation, an excipient (e.g., corn starch) was added to each of the herbal condensate. The amount of corn starch which was added to each of the condensates varied depending on the stability of the condensates. The end product of STA-4, which was in the form of granules, was about half of the weight of that of STA-36, even though both were derived from the same amount of raw materials. The reduction in total gram weight in STA-4, while maintaining the same or better therapeutic effects on immunological disorders as STA-36, constituted another improvement from STA-36, because it meant that the patients would not have to take in twice amount of the herbs to get the same or better therapeutic effects.

The following examples are illustrative, and should not be viewed as limiting the scope of the present invention. Reasonable variations, such as those occur to reasonable artisan, can be made herein without departing from the scope of the present invention.

EXAMPLE 1

Quality Control of the Herbs Used In STA-36 and STA-4 By High-performance Liquid Chromatography The present invention used HPLC techniques to ensure the quality of the herbs was well under control. Three HPLC methods were developed to accommodate the chemical and physiological characteristics of each herb. The three HPLC methods were described as follows:

(A) Method 1 of the HPLC Analysis

Method 1 used a precolumn Lichrospher RP-18 endcapped (5 μm, 4.0 ID×10 mm, Merck), and a Cosmosil 5C18-MS column (5 μm, Nacalai tesque 5C18-MS, 4.6 ID×250 mm) at room temperature. The mobile phase of the column was a gradient containing (A) $H_2O:KH_2PO_4:10\%$ $H_3PO_4$ (1000 ml:2.72 g:1 ml, v/w/v), (B) $CH_3CN$, (C) $H_2O$, and (D) $CH_3OH$. The elution gradient was described in Table 4. The flow rate was 1.0 ml/min. The detection wavelength was 250 nm. The total retention time of the analysis was 60 minutes.

TABLE 4

Mobile Phase Gradient of Method 1

| Time | (A) | (B) | (C) | (D) |
|---|---|---|---|---|
| Initial | 90 | 10 | 0 | 0 |
| 30 | 75 | 25 | 0 | 0 |
| 40 | 65 | 35 | 0 | 0 |
| 55 | 0 | 75 | 25 | 0 |
| 60 | 0 | 10 | 90 | 0 |

Post run: 15 min.

(B) Method 2 of the HPLC Analysis

Method 2 of the HPLC analysis used a precolumn Lichrospher RP-18 endcapped (5 μm, 4.0 ID×10 mm, Merck), and a Cosmosil 5C18-MS column (5 μm, Nacalai tesque 5C18-MS, 4.6 ID×250 mm) at 35° C. The mobile phase of the column was a gradient containing (A) 10 mM $KH_2PO_4$+10 mM $K_2HPO_4$+0.01% $H_3PO_4$ ($KH_2PO_4$:$K_2HPO_4$: 10%$H_3PO_4$:$H_2O$=1.36 g:1.74 g:1 ml:1000 ml), (B) $CH_3CN$, (C) $H_2O$, and (D) $CH_3OH$. The elution gradient was described in Table 5. The flow rate was 1.0 ml/min. The detection wavelength was 260 nm. The total retention time of the analysis was 60 minutes.

TABLE 5

Mobile Phase Gradient of Method 2

| Time (min) | (A) | (B) | (C) | (D) |
|---|---|---|---|---|
| Initial | 100 | 0 | 0 | 0 |
| 25 | 60 | 0 | 20 | 20 |
| 30 | 20 | 0 | 20 | 60 |
| 35 | 100 | 0 | 0 | 0 |

Post run: 15 min.

(C) Method 3 of the HPLC Analysis

Method 3 of the HPLC analysis used a precolumn Lichrospher RP-18 endcapped (5 μm, 4.0 ID×10 mm, Merck), and a Cosmosil 5C18-MS column (5 μm, Nacalai tesque 5C18-MS, 4.6 ID×250 mm) at 35° C. The mobile phase of the column was a gradient containing (A) $H_2O:KH_2PO_4$ (1000 ml: 2.72g, v/w), (B) $CH_3CN$, (C) $H_2O$, and (D) $CH_3OH$. The elution gradient was described in Table 6. The flow rate was 1.0 ml/min. The detection wavelength was 203 nm. The total retention time of the analysis was 60 minutes.

TABLE 6

Mobile Phase Gradient of Method 3

| Time (min) | (A) | (B) | (C) | (D) |
|---|---|---|---|---|
| Initial | 80 | 20 | 0 | 0 |
| 40 | 65 | 35 | 0 | 0 |
| 55 | 0 | 80 | 20 | 0 |
| 60 | 0 | 20 | 80 | 0 |

Post run: 15 min.

The HPLC analysis of the herbs used in STA-3 composition, which includes the method, major marker(s), and detection wavelength of each herb, are summarized in Table 7. The HPLC chromatograms of the STA-36 herbs are shown in FIGS. 1–5.

TABLE 7

HPLC Analysis of Herbs Used in STA-36

| Herbal Name | HPLC Analytical Method | Marker(s) | Retention Time (min) | Wavelength (nm) |
|---|---|---|---|---|
| Ophiopogon | Method 1 | 6115-1 | 11.5 | 214 |
|  |  | 6115-2 | 13.0 | 214 |
| Pinellia | Method 2 | Adenine | 14.8 | 250 |
|  |  | Guanosine | 17.0 | 250 |
| *Radix Glycyrrhizae* | Method 1 | Glycyrrhizin | 46.4 | 250 |
| American Ginseng | Method 3 | Ginsenoside Rb$_1$ | 37.5 | 203 |
| Lantern Tridax | Method 1 | FY-1 | 28.0 | 250 |
|  |  | FY-2 | 31.6 | 250 |
|  |  | FY-3 | 33.5 | 250 |
|  |  | FY-4 | 18.3 | 250 |

Before HPLC analysis, 0.5 g of the herbal sample was mixed with 20 ml solution containing 70% of methanol. The sample solution was sonicated for 15 min at room temperature and placed in a rotating water bath at 40° C. for 20 min with the rotation speed set at 160 rpm. The sample solution was then left to sit for about 30 min to allow the debris to precipitate. Ten (10) ml of the supernatant was then pipetted out and passed through a 0.45 μm filter. The filtrate was ready for HPLC analysis. Twenty (20) μl of the filtrate was taken for HPLC analysis.

Figure 1:
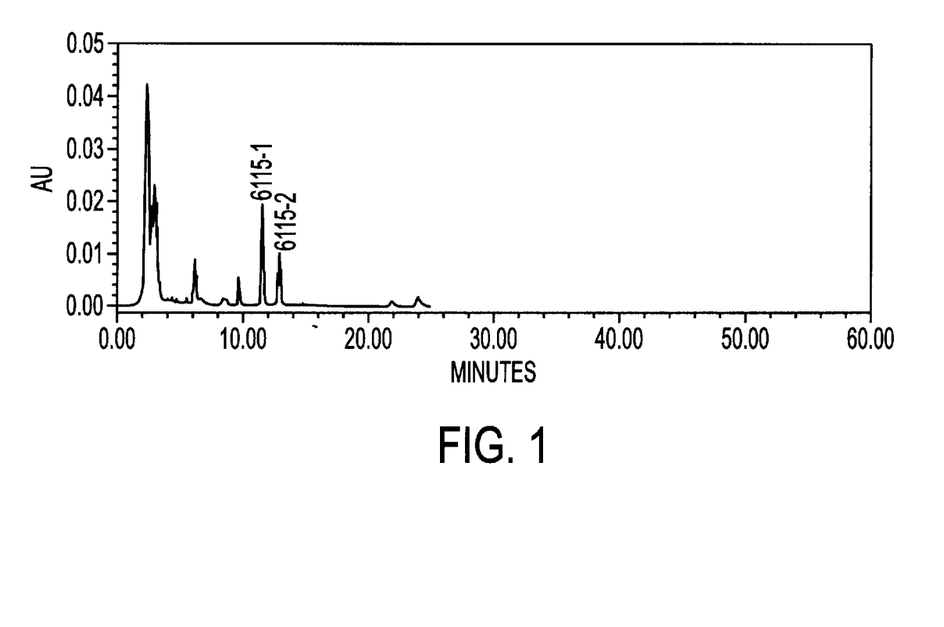

Results:

The HPLC chromatogram of ophiopogon is shown in FIG. 1. As shown in Table 7, method 1 of the HPLC analysis was used to detect ophiopogon at 214 nm wavelength. Two distinctive peaks, 6115-1 and 6115-2, were identified on the ophiopogon HPLC chromatogram. 6115-1 had a retention time of 11.5 min. 6115-2 had a retention time of 13 min. Although the chemical components in these two peaks were not yet identified, they could be used for the purpose of ensuring the quality of ophiopogon.

Figure 2:
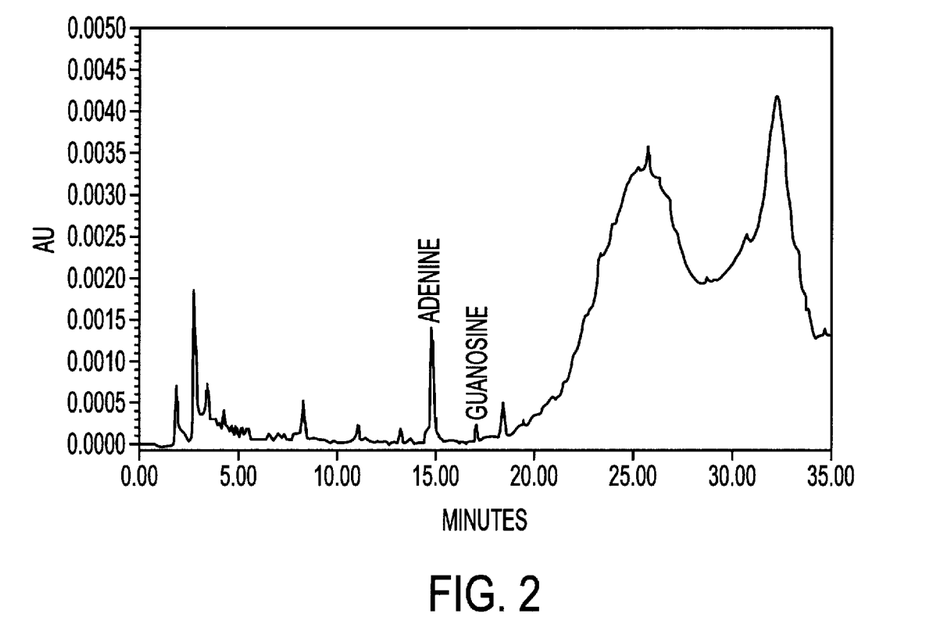

The HPLC chromatogram of pinellia is shown in FIG. 2. As shown in Table 7, using method 2 of the HPLC analysis to detect pinellia at 250 nm wavelength, pinellia had shown two distinctive chemical markers, i.e., adenine and guanosine, both are constituents of nucleic acids. Adenine also has effect of elevating serum aldolase. Adenine had a retention time of 14.8 min. Guanosine had a retention time of 17 min.

Figure 3:
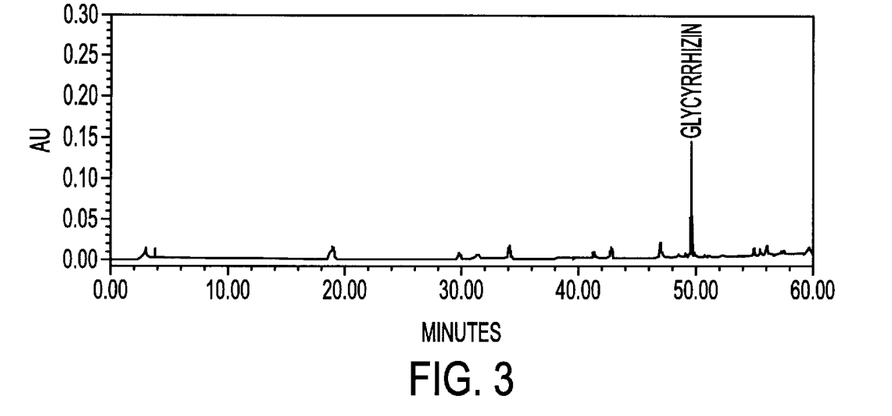

The HPLC chromatogram of *Radix glycyrrhizae* is shown in FIG. 3. As shown in Table 7, using method 1 of the HPLC analysis to detect *Radix glycyrrhizae* at 250 nm wavelength, a chemical marker "glycyrrhizin" was found in the *Radix glycyrrhizae* HPLC chromatogram. Glycyrrhizin ($C_{42}H_{62}O_{16}$) is a very sweet substance. It is known to have detoxification, anti-inflammation, and haemolysis effects, and has been used to treat Addison's disease. The retention time for glycyrrhizin is 46.4 min.

Figure 4:
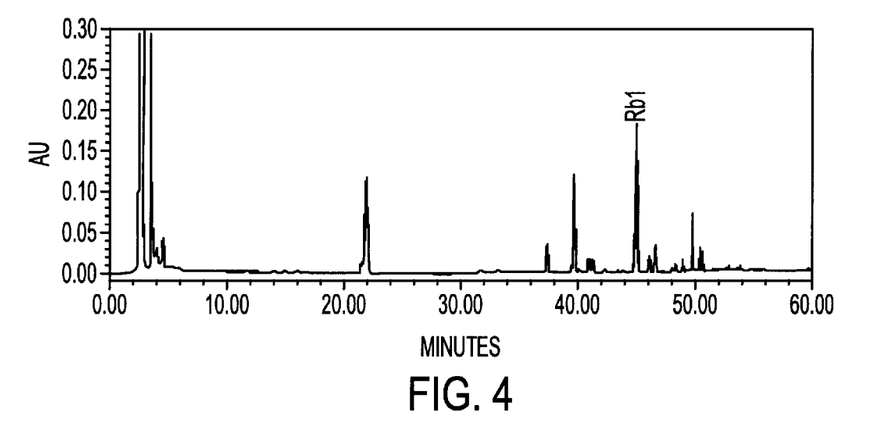
FIG. 4 shows an HPLC chromatogram of American ginseng. A chemical marker, ginsenoside $Rb_1$ ($Rb_1$), was detected at 203 nm wavelength using method 3 of the HPLC analysis. $Rb_1$ has a retention time of 37.5 min.

The HPLC chromatogram of American ginseng is shown in FIG. 4. As shown in Table 7, using method 3 to detect American ginseng at 203 nm wavelength, a chemical marker "ginsenoside Rb$_1$" was found in the American ginseng HPLC chromatogram. Ginsenoside Rb, has medicinal effects on dilating blood vessel, relieving fatigue, and avoiding haemolysis.

Figure 5:
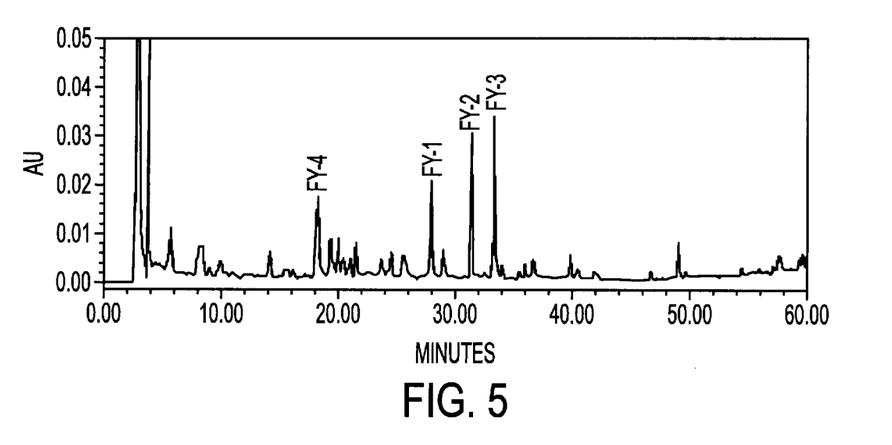

The HPLC chromatogram of lantern tridax is shown in FIG. 5. As indicated in Table 7, using method 1 of the HPLC analysis to detect lantern tridax at 250 nm wavelength, four (4) distinctive peaks, FY-1 to FY-4, were identified. FY-1 had a retention time of 28.0 min. FY-2 had a retention time of 31.6 min. FY-3 had a retention time of 33.5 min. FY-4 had a retention time of 18.3 min. Due to the consistent appearance of these four peaks, even though the chemical contents associated with these four peaks were still not yet identified, they could be used for the purpose of identifying and ensuring the quality of lantern tridax.

EXAMPLE 2

Thin-layer Chromatography (TLC) Characterization of Raw Licorice, Ophiopogon, Pinellia, and Lantern tridax In addition to HPLC, some of the herbs used in the STA-36 and STA-4 compositions, including raw licorice, ophiopogon, pinellia, and lantern tridax, can be characterized by thin-layer chromatography (TLC) methods.

The TLC method used a stationary phase of silica gel 60 F254 (which was bound to the TLC plate) and three mobile phase (or developing) solvents, depending upon the characteristics of the herbs. The first solvent contained ethyl acetate, 4 N ammonia water, and ethanol in a volume ratio of 4:1:2 (v/v/v). This first solvent was particularly useful for characterizing *Radix glycyrrhizae*. The second solvent contained butanol, 4 N ammonia water, and ethanol in a volume ratio of 5:2:1 (v/v/v). This second solvent was particularly useful for characterizing ophiopogon and American ginseng. The third solvent contained chloroform ($CHCl_3$) and methanol at a volume ratio of 5:1 (v/v). This third solvent was particularly useful for characterizing lantern tridax. For each TLC determination, 5 μl of sample was spotted at the starting point of the TLC plate. The plate was placed in a TLC chamber within which the developing solvent was applied. The solvent was allowed to migrate up to 9 cm. The results of the TLC determination were described as follows:

(A) Raw Licorice

Raw licorice was analyzed by TLC using a stationary phase of silica gel 60 F254 attaching to a TLC plate, and a developing solvent containing ethyl acetate:4N ammonia water:Ethanol=4:1:2 (v/v/v). After the application of the sample, the TLC plate was placed into the TLC chamber which contained the developing solvent with the upper liquid mark not to exceed the sample application point. The solvent was allowed to migrate up to 9 cm from the sample application point. Then, the TLC plate was taken out of the TLC chamber and air dried. The dried TLC plate was sprayed with a spraying reagent containing vanillin/$H_2SO_4$. The plate was then activated under heat at 105° C. for two (2) minuets. A yellow spot which represented *Radix glycyrrhizae* appeared on the plate at approximately Rf=0.5. Rf (the distance [cm] between the spot and the sample application point)/total migration distance [i.e., 9 cm]).

(B) Ophiopogon

Ophiopogon was analyzed by TLC using a stationary phase of Silica gel 60 F254 attaching to a TLC plate and a developing solvent containing butanol:4N ammonia water:ethanol=5:2:1 (v/v/v). After the application of the sample, the TLC plate was placed into the TLC chamber which contained developing solvent with the upper liquid mark not to exceed the sample application point. The solvent was allowed to migrate up to 9 cm from the sample application point. Then, the TLC plate was taken out of the TLC chamber and air dried. The dried TLC plate was sprayed with a spraying reagent containing vanillin/$H_2SO_4$. The plate was then activated under heat at 105° C. for two (2) minuets. A brown spot which represented ophiopogon appeared on the plate at approximately Rf=0.4.

(C) American Ginseng

American ginseng was analyzed by TLC using a stationary phase of Silica gel 60 F254 attaching to a TLC plate and a developing solvent containing butanol:4N ammonia water:ethanol=5:2:1 (v/v/v). After the application of the sample, the TLC plate was placed into the TLC chamber which contained the developing solvent with the upper liquid mark not to exceed the sample application point. The solvent was allowed to migrate up to 9 cm from the sample application point. Then, the TLC plate was taken out of the TLC chamber and air dried. The dried TLC plate was sprayed with a spraying reagent containing vanillin/$H_2SO_4$. The plate was then activated under heat at 105° C. for two (2) minuets. A purplish spot which represented American ginseng appeared on the plate at approximately Rf=0.3.

(D) Lantern Tridax

Lantern tridax was analyzed by TLC using a stationary phase of Silica gel 60 F254 attaching to a TLC plate and a developing solvent containing chloroform:methanol=5:1 (v/v). After the application of the sample, the TLC plate was placed into the TLC chamber which contained the developing solvent with the upper liquid mark not to exceed the sample application point. The solvent was allowed to migrate up to 9 cm from the sample application point. Then, the TLC plate was taken out of the TLC chamber and air dried. The dried TLC plate was placed under a UV detector and detected at 366 nm wavelength. A pale yellow fluorescent spot which represented lantern tridax appeared on the plate at approximately Rf=0.3.

EXAMPLE 3

Methods of Determining IgG, IgE, IL-4 and IFN-γ In Animals

The effects of the STA-36 and STA-4 herbal composition as well as individual herbs on suppression of allergen-induced immunoglobulin G (IgG), immunoglobulin E (IgE), interleukin-4 (IL-4), and interferon γ (IFN-γ) were investigated using BALB/c mice sensitized with D.P. (Dermatophagoides pteronyssimus) allergen "Der p 5". Dermatophagoides pteronyssimus is the house dust mite which acts as an antigen and produces an allergic asthmatic reaction in atopic person.

Experimental Design:

(A) Animals

Female BALB/c mice aged between 4 and 6 weeks and weighed about 20 g were obtained from the National Animal-breeding Center, Republic of China and used in the studies. Mice were age- and sex- matched for each experiment.

(B). Allergen Derp5 (Dermatophagoidespteronyssinus group 5 allergen) Purification pGEX-2T plasmid was used to express Der p 5-glutathion S-transferase (GST) in *E. coli*. The molecular weight of the fusion protein was about 42 kD. The protein was purified by glutathione-conjugated agarose gel column chromatography. A single colony of the Der p 5-GST positive-bacterial strain was selected by growing the transfected *E. coli* on LB broth containing Ampicillin (100 μg/ml). The Der p 5-GST positive *E. coli* colony was further cultured to produce substantial amount of Der p 5-GST. Then, the bacterial culture was collected and centrifuged. The supernatant was discarded, and the pellet was washed with TBS (pH 7.5) and collected in a centrifuge tube. hImediately following the TBS wash, 0.1 M phenylmethylsulfonyl fluoride was added to the pellet, followed by the addition of DNase I, Tween 20, and lysozyme. The pellet was lyzed by the freeze-and-thaw process to release Der p 5+GST protein. Subsequently, EDTA was added to the cell lysate, which was then centrifuged. The pellet was discarded, and the supernatant was poured onto a glutathione-conjugated agarose gel adsorption column where Der p 5-GST protein was adsorbed onto the column. The column was washed first by TBS buffer solution at 4° C., and then by reduced glutathione in Tris-base (pH 8.0) to separate the Der p 5-GST from the agarose gel column. The purity of the Der p 5-GST protein was confirmed by SDS-PAGE. The quantity of the protein was measured by conventional protein analytical methods.

(C) Animal Sensitization

BALB/c mice were initially intraperitoneally sensitized with 10 μg of Dermatophagoides pteronyssimus group 5 ("Der p 5") allergen and 4 mg of aluminium hydroxide (Wyeth Pharmaceuticals, Punchbowl, Australia). Seven (7) days after the first sensitization, mice, except the placebo control group, were fed with STA-36 and STA-4 herbal compositions until the end of the twenty-first day.

At the end of the twenty first day, the mice were given a second booster injection of Der p 5. Forty eight (48) hours after the second booster injection, mice were placed in a round plastic container where the mice were further challenged by 0.1% Der p 5 spray.

Several hours after the challenge, the mouse was anaesthetized using 100 mg/ml phenobarbital. Blood was collected from the tail vein or heart. The blood was allowed to sit at room temperature for 1 hour and then centrifuged at 1000 rpm for about 10 minutes to collect serum, which was stored at −80° C. for ELISA (see below) analysis of IgE and IgG2a. The fluid collected from washing the pulmonary alveoli was centrifuged at 1000 rpm for 10 minutes. The supernatant of the fluid was used for analysis of cytokine, interleukin-4 (IL-4) and interferon-γ (IFN-γ). The pellet of the fluid (containing the cells) were re-dissociated using PBS and proceed with cytospin count for inflammatory cells.

(D) ELISA Determination of Der p 5-specific IgG and IgE

The amount of Der p 5-specific IgG and IgE were determined by Enzyme Linked Immunosorbent Assay (ELISA). High protein high binding microwell plates (Costar, No. 3590) were coated with 100 μl (10 mg/ml) purified Der p 5 diluted in coating buffer (PBS solution containing 3% BSA, pH 7.4) to a concentration of 5 μg/ml. After overnight incubation at 4° C., plates were washed three times in PBS solution (pH 7.4) containing 0.05% Tween 20 and blocked with 3% (wt/vol) BSA-PBS buffer for 2 hr at 25° C.

Sera were used at 1:100 dilution for IgG measurement and 1:10 dilution for IgE measurement in duplicate. After overnight incubation at 4° C., either biotin-conjugated monoclonal rat anti-mouse IgE mAb (PharMinge 02122D), or rat anti-mouse IgG mAb (PharMinge, 02022D) diluted in 0.05% gelatin buffer, was added for an additional 2 hours.

Avidin-alkaline phosphatase (1:1000) (Strptavidin-AP, PharMinge 13043E) was then added and incubated for 1 hour at 25° C., followed by six (6) washes. The color reaction was developed with the addition of phosphatase substrate p-nitrophenyl phosphate, disodium (pNPP alkaline phosphatase substrate, Sigma N-2770). Plates were read in a microplate autoreader (ELISA reader, Dynex MRX) at 405 nm. Readings were referenced to commercial isotypes standards which were mouse anti-TNP mAb, IgG1 (107.3), IgG2a (G155–178), and IgE (IgE-3).

(E) ELISA Determination of cytokines (IL-4 and IFN-γ)

High protein high binding microwell plates (Costar, No. 3590) were coated with purified anti-cytokine antibody (for IL-4, 2 μg/ml of IL-4 antibody from PharMinge 18191D was used; for IFN-γ, 3 μg/ml of IFN-γ antibody, PharMinge 18181D was used). The plates were coated with PBS solution containing 3% BSA, pH 7.4 and then washed with PBS solution containing 0.05% Tween-20, pH 7.4.

One hundred (100) μl of the supernatant from the fluid of pulmonary alveoli were then added to the microwells, together with cytokine standard solution, for overnight reaction at 4° C. Then, 100 μl of biotin-anti-mouse-IL-4 (PharMinge 18042D, 1 μg/ml) or biotin-anti-mouse-IFN-γ (PharMinge 18112D, 1 μg/ml) were added to the microwells. After two (2) hours of reaction, 100 μl of avidin-alkaline phosphatase (1:1000) (streptavidin-AP, PharMinge 13043E) were added to microwells with vibration for 1 hour. Two hundred (200) μl of phosphatase substrate p-nitrophenyl phosphate, disodium (pNPP alkaline phosphatase substrate, Sigma N-2770) were added to microwells for color development. Plates were read in a microplate autoreader (ELISA reader, Dynex MRX) at 405 nm.

(F) Measuring of Lung Function.

After iv injection of 100 mg/ml of phenobarbital to the mouse, a PE 50 tube was inserted into the trachea. The tube was connected to a pressure detection device to measure the change in respiratory pressure during inhalation and exhalation. Another PE 50 tube was inserted into the esophagus to measure the esophagus pressure as substitute for transpulmonary pressure (TPP). When the signal of pressure was transmitted to Bio-Recorder BR8000, the signal was amplified and converted into volume of breath and transpulmonary pressure to calculate the trachea pressure. During the experiment, a needle was maintained at the tail vein to provide for acetylcholine (Ach) injection so as to induce change in trachea pressure.

4. Statistics.

All of the data contained in the experiments were calculated as "mean±SEM." Trachea resistance change induced by acetylcholine after converted to PC 100 was measured as μg/kg. Ig E and Ig $G_{2a}$ measurement were shown based upon value of optical absorption. The unpaired student's t test was used to determine the significance of the differences among the groups. A $p<0.05$ was used to indicate statistical significant difference.

EXAMPLE 4

Effects of Aqueous Extraction of the Herbs on IgG and IgE

Various aqueous extraction methods were tested on American ginseng and lantern tridax to determine the optimal form of aqueous extract to be used in the herbal composition.

Figure 6:
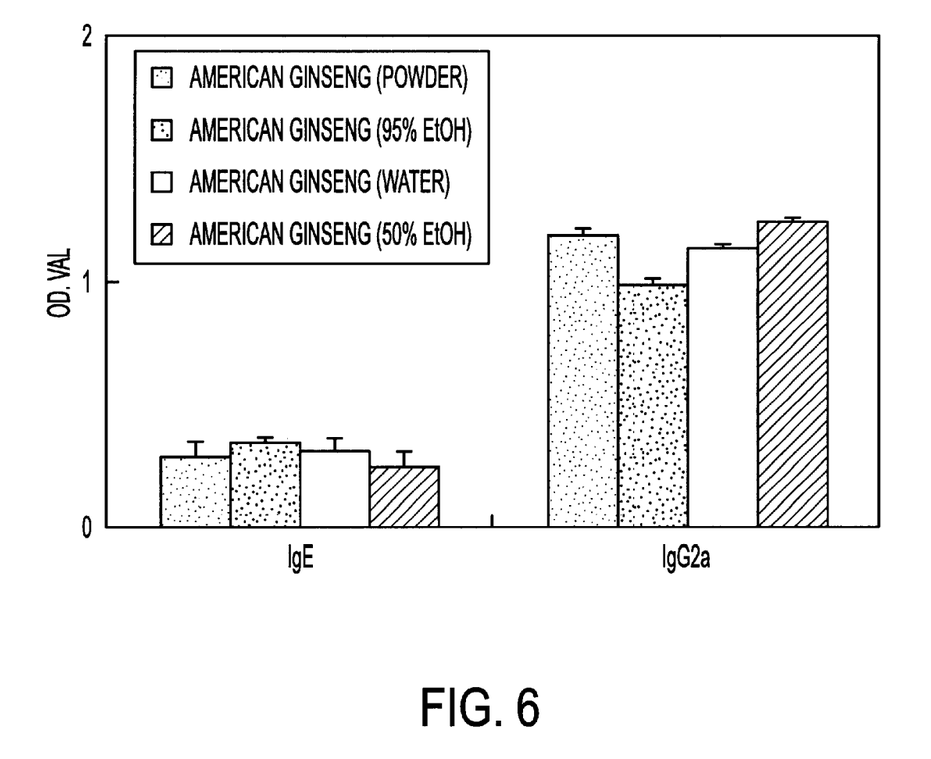
FIG. 6 compare the effects of American ginseng in the form of (1) powder, (2) aqueous extract in 95% alcohol, (3) aqueous extract in water, and (4) aqueous extract in 50% alcohol, on the level of $IgG_{2a}$ and IgE. Values are means±SEM. The figure indicates that American ginseng extracted by 50% alcohol produced slightly better effects in terms of decreasing IgE and increasing IgG, than water extract.

American ginseng in (1) powder, (2) 95% alcohol extract, (3) water extract, and (4) 50% alcohol extract was tested for its medicinal effects on suppression of IgE and $IgG_{2a}$. As shown in FIG. 6, American ginseng extracted with 50% alcohol produced the best IgE suppression effect, even though its effect on $IgG_{2a}$ reduction was not as good as that extracted in 95% alcohol. Because antigen-induced immunological disorders were primarily IgE mediated diseases, it appears that using 50% alcohol extraction for American ginseng in the herbal composition should provide the best IgE reduction result for the composition. However, when the granules produced from the alcohol extract of American ginseng were added to the rest of the granules, the granules produced from the water extract of American ginseng provided better effects on both IgE inhibition and IgG elevation. Thus, in the STA-4 composition, the American ginseng was extracted from water.

Figure 7:
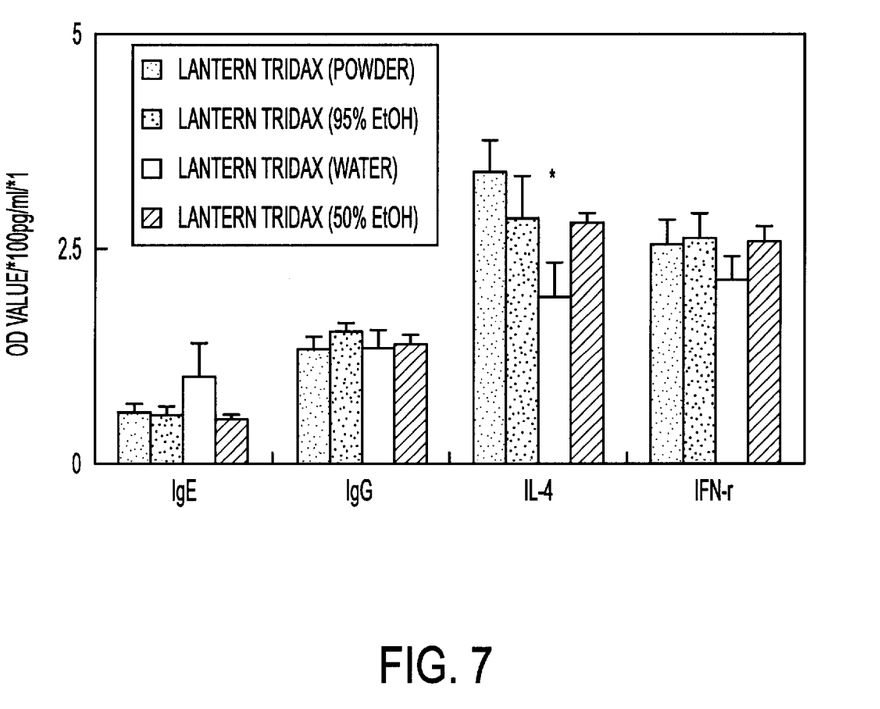
FIG. 7 compares the effects of lantern tridax in the form of (1) powder, (2) aqueous extract in 95% alcohol, (3) aqueous extract in water, and (4) aqueous extract in 50% alcohol, on the level of IgE, $IgG_{2a}$, IL-4, and IFN-γ. Values are means±SEM. * indicates significant difference from control. Results indicate that 50% ethanol extract of lantern tridax was most effective on inhibiting IgE and increasing IgG.

Lantern tridax in (1) powder, (2) 95% alcohol extract, (3) water extract, and (4) 50% alcohol extract was also tested for its medicinal effects on suppression of IgE, $IgG_{2a}$, IL-4 and IFN-γ. As shown in FIG. 7, lantern tridax extracted with 50% alcohol produced the best IgE and $IgG_{2a}$ suppression effect, even though the water extract of lantern tridax had demonstrated the best suppression effect on IL-4 and IFN-γ. Nevertheless, because the water extract of lantern tridax had induced blood clotting in animals during the studies, it was not under consideration for use in humans.

EXAMPLE 5

Comparison of the Effects of STA-36 and STA-4 on IgE, IgG, IL-4, IFN-γ and Lung Functions A comparative study between the medicinal effects of herbal compositions of STA-36 and STA-4 on IgE, IgG, IL-4, and IFN-γ, as well as on lung functions was conducted in experimental animals as described in Example 3 (supra). The results of this study are shown in FIGS. 8–10.

Figure 8:
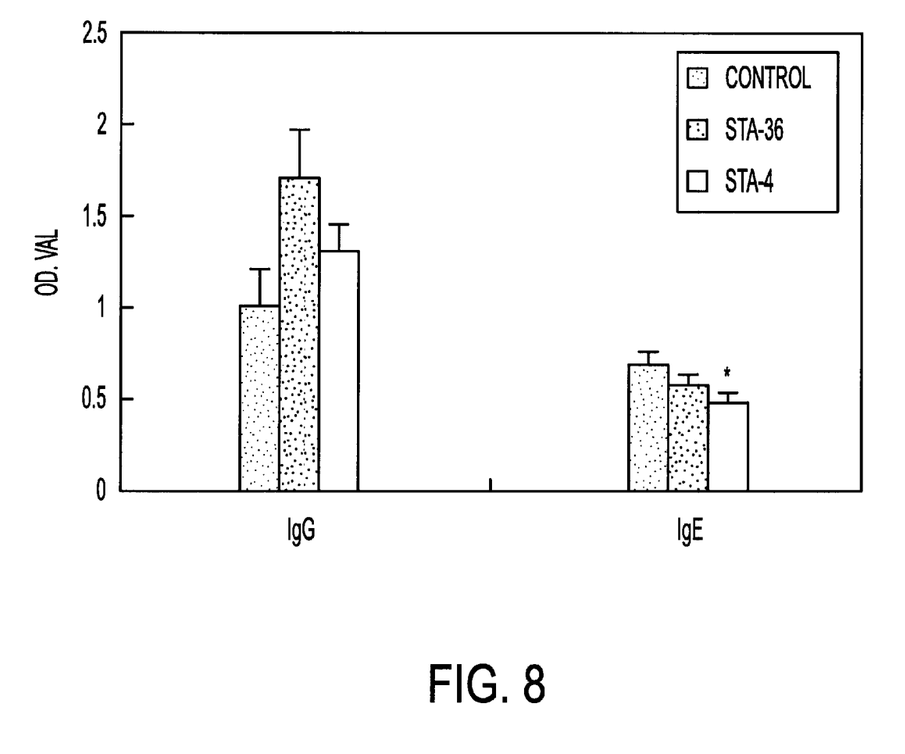

FIG. 8 shows a comparative study of the effects of the herbal compositions of STA-36 and STA-4 on IgG and IgE in mice. As shown in FIG. 8, both the herbal compositions of STA-36 and STA-4 demonstrated suppression of IgE, as compared with the control, with the effect of STA-4 much greater than that of STA-36. The inhibitory effect on IgE by STA-4 was statistically significant over the control. However, neither STA-36 nor STA-4 demonstrated an inhibitory effect on IgG. In fact, on the contrary, the level of IgG increased in both STA-36 and STA-4 treatment groups, as compared with the control.

Figure 9:
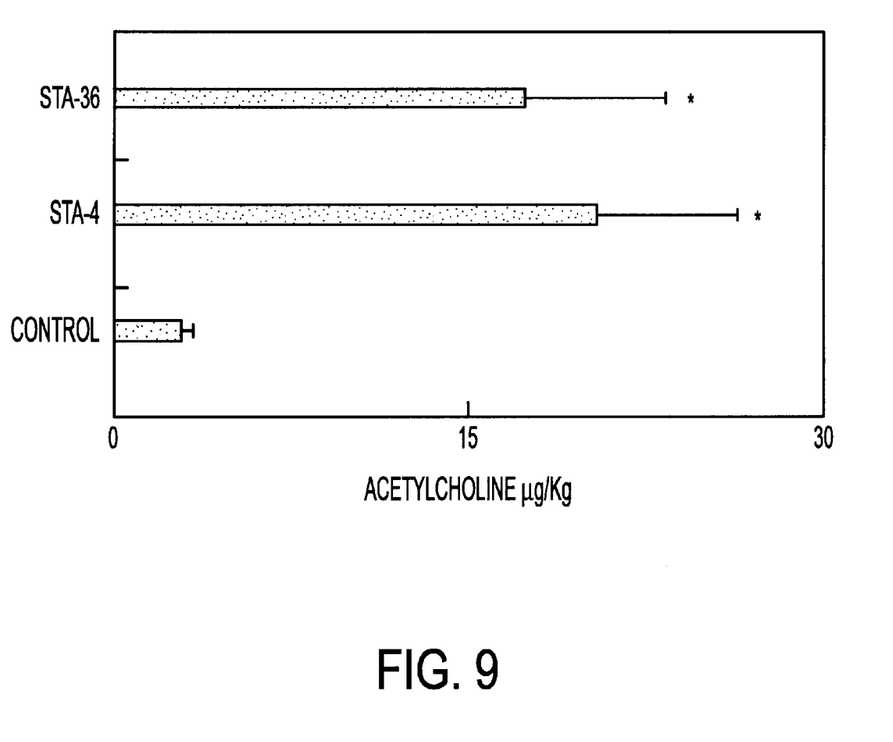

FIG. 9 shows the effects of STA-36 and STA-4 on lung functions of the mice. Both STA-36 and STA-4 show significant improvement on lung functions than the control ($p<0.05$). Among the two, STA-4 shows better improvement on lung functions than STA-36, although the values between STA-4 and STA-36 were not significantly different probably due to insufficient numbers (n) of animals in each experimental group.

Figure 10:
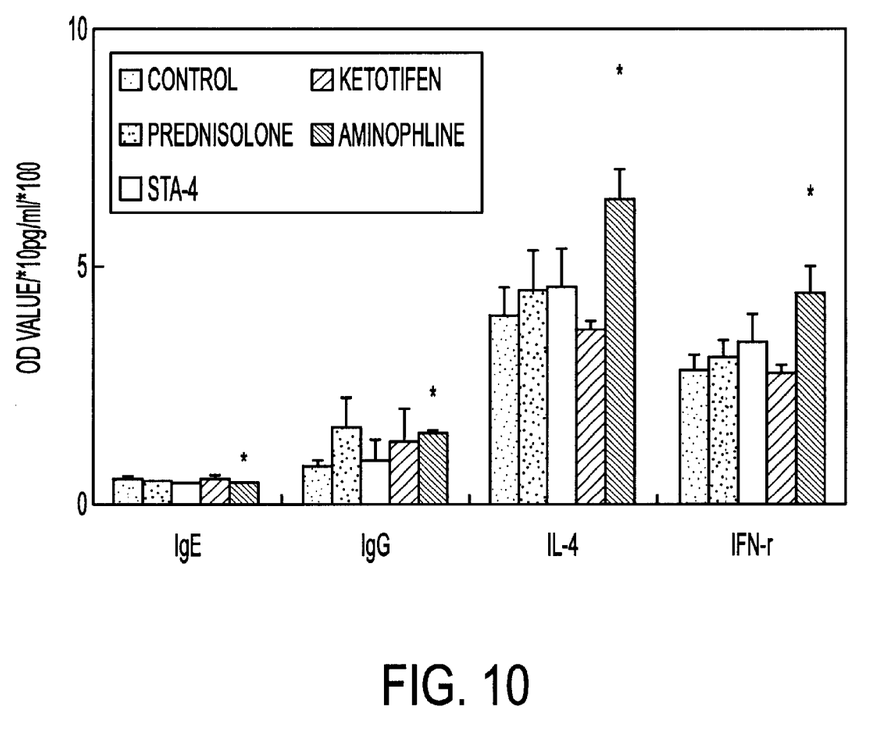
FIG. 10 compares the effects STA-4 on IgE, IgG, IL-4, and IFN-γ with those of the conventional drugs (for treating asthma) including Ketotifen, Prednisolone, and Aminophline. Values are means±SEM. * indicates significant difference from control. The results of this study indicate that STA-4 significantly lowered the level of IgE, but significantly increased the level of $IgG_{2a}$, Il-4 and IFN-γ.

FIG. 10 compares the effects of STA-4 with conventional asthma drugs, i.e., ketotifen, prednisolone, and aminophline on IgE, IgG, IL-4 and IFN-γ. The results show hat only STA-4 demonstrated significant decreased in IgE and significant increase in IgG, IL-4, and IFN-γ, thus, suggesting that STA-4 possessed better therapeutic effects in treating asthma than ketotifen, prednisolone, and aminophline.

The results in FIG. 10 also suggests that the therapeutic effects of STA-4 might be different from the conventional mechanism where the drug suppressed IL-4 synthesis which then indirectly decreased the level of IgE. In the present case, both IL-4 and IFN-γ increased substantially after the intake of STA-4 so that the reduction in IgE was not due to decrease in IL-4. On the contrary, the amount of IFN-γ (produced and secreted by TH1 cell) increased significantly after the treatment of STA-4. IFN-γ stimulates B cells to synthesize and secrete $IgG_{2a}$, which explained why the amount of $IgG_{2a}$ increased during the STA-4 treatment. Thus, it is postulated that the STA-4 effects were at least partially derived from $IgG_{2a}$, which, upon second contact with the allergens, interacted with the allergens so as to reduce the allergic reaction.

EXAMPLE 6

Test of Toxicity of the Herbal Compositions of STA-36 and STA-4

The herbal compositions were tested for toxicity based on a 28-day sub-acute oral toxicity study in which the mortality, ophthalmologic examination, clinical signs, and gross necropsy were determined. The results are shown in Tables 8–10:

TABLE 8

Mortality of Mice After Intake of STA-36 and STA-4

|  | 2% Tween-80 Aqueous Solution | STA-36 | STA-4 |
| --- | --- | --- | --- |
| Dose (mg/kg/day) |  | 5000 | 5000 |
| Sex | Male | Male | Male |
| Number of mice | 10 | 10 | 10 |
| Mortality | 0/10 | 0/10 | 0/10 |

TABLE 9

Ophthalmologic Examination and Clinical Signs of Mice After Intake of STA-36 and STA-4

|  | 2% Tween-80 Aqueous Solution | STA-36 | STA-4 |
| --- | --- | --- | --- |
| Dose (mg/kg/day) |  | 5000 | 5000 |
| Sex | Male | Male | Male |
| Number of mice | 10 | 10 | 10 |
| Before Initiation (Day 0) | 0/10 | 0/10 | 0/10 |
| Before necropsy (Day 28) | 0/10 | 0/10 | 0/10 |
| Clinical signs | 0/10 | 0/10 | 0/10 |

TABLE 10

Gross Necropsy After Intake of STA-36 and STA-4

|  | 2% Tween-80 Aqueous Solution | STA-36 | STA-4 |
| --- | --- | --- | --- |
| Dose (mg/kg/day) |  | 5000 | 5000 |
| Sex | Male | Male | Male |
| Number of mice | 10 | 10 | 10 |
| Organs abnormal | 0/10 | 0/10 | 0/10 |

The results of Tables 8–10 demonstrated that both STA-36 and STA-4 showed no sign of sub-acute toxicity in the study.

Having described the invention in detail and by reference to the preferred embodiments it will be apparent to those skilled in the art that modifications and variations are possible without departing from the scope of the invention as defined in the following appeded claims.

We claim:

1. A pharmaceutical composition comprising:
   an aqueous extract of *Tuber ophiopogonis*;
   an aqueous extract of *Tuber pinelliae*;
   an aqeous extract of *Radix glycyrrhizae*;
   an aqueous extract of *Herba tridacis procumbentis*; and
   an aqueous extract of *Radix pancis quinquefolii*.

2. The pharmaceutical composition according to claim 1, wherein each of said aqueous extracts of *Tuber ophiopogonis, Tuber pinelliae, Radix glycyrrhizae, Herba tridacis procumbentis*, and *Radix pancis quinquefolii* are separately filtered and condensed to form each of condensate of *Tuber ophiopogonis, Tuber pinelliae, Radix glycyrrhizae, Herba tridacis procumbentis*, and *Radix pancis quinquefolii*.

3. The pharmaceutical composition according to claim 2, wherein each of said condensates of *Tuber pinelliae, Radix glycyrrhizae, Herba tridacis procumbentis*, and *Radix pancis quinquefolii* is separately granulated to form individual granules; wherein said granules from *Tuber pinelliae, Radix glycyrrhizae, Herba tridacis procumbentis*, and *Radix pancis quinquefolii* and said condensate of *Tuber ophiopogonis* are mixed together to form mixed granules.

4. The pharmaceutical composition according to claim 3, wherein an excipient is added to each of said condensates of *Tuber pinelliae, Radix glycyrrhizae, Herba tridacis procumbentis*, and *Radix pancis quinquefolii* before granulation.

5. The pharmaceutical composition according to claim 4, wherein said excipient is corn starch.

6. The pharmaceutical composition according to claim 1, wherein *Tuber ophiopogonis, Tuber pinelliae, Radix glycyrrhizae, Herba tridacis procumbentis*, and *Radix pancis quinquefolii* are at a weight ratio of about 3:2:1:1:1.

7. The pharmaceutical composition of claim 1, wherein said aqueous extract of *Tuber ophiopogonis* is a water extract of *Tuber ophiopogonis*.

8. The pharmaceutical composition of claim 1, wherein said aqueous extract of *Tuber pinelliae* is a water extract of *Tuber pinelliae*.

9. The pharmaceutical composition of claim 1, wherein said aqueous extract of *Radix glycyrrhizae* is a water extract of *Radix glycyrrhizae*.

10. The pharmaceutical composition of claim 1, wherein said aqueous extract of *Herba tridacis procumbentis* is an alcohol extract of *Herba tridacis procumbentis*.

11. The pharmaceutical composition of claim 10, wherein said alcohol extract of *Herba tridacis procumbentis* is a 50% alcohol extract.

12. The pharmaceutical composition of claim 1, wherein said aqueous extract of *Radix pancis guinquefolii* is water extract of *Radix pancis quinquefolii*.

13. The pharmaceutical composition according to claim 2, wherein a solid content of said condensate of *Tuber ophiopogonis* is about 20–30% by weight of *Tuber ophiopogonis*; a solid content of said condensate of *Tuber pinelliae* is about 15–25% by weight of *Tuber pinelliae;* a solid content of said condensate of *Radix glycyrrhizae* is about 15–25% by weight of *Radix glycyrrhizae*, a solid content of said condensate of *Radix pancis quinquefolii* is about 19–29% by weight of *Radix pancis quinquefolii*, and a solid content of said condensate of said *Herba tridacis procumentis* is about 5–10% of *Herba tridacis procumbentis*.

14. The pharmaceutical composition according to claim 3, wherein said granules of *Tuber pinelliae* is about 20–30% by weight of *Tuber pinelliae* raw material; said granules of *Radix glycyrrhizae* about 16–26% of *Radix glycyrrhizae* raw material; said granules of *Radix pancis quinquefolii* is about 27–37% by weight of *Radix pancis quinquefolii* raw material; and said granules of *Herba tridacis procumbentis* is about 37–47% by weight of *Herba tridacis procumbentis* raw material.

15. The pharmaceutical composition according to claim 1, wherein said pharmaceutical composition treats patients with immunological disorders.

16. The pharmaceutical composition according to claim 15, wherein said immunological disorders comprises at least one selected from the group consisting of allergic rhinitis, allergic conjunctivitis, allergic asthma, atopic eczema, atopic dermatitis, food allergy, hyper IgE syndrome, and rheumatoid arthritis.

17. A method for preparing a pharmaceutical composition according to claim 1 comprising:

extracting *Tuber ophiopogonis* in water by decocting; said water extract of *Tuber ophiopogonis* being filtered and concentrated to form a condensate of *Tuber ophiopogonis*;

extracting *Tuber pinelliae* in water by decocting; said water extract of *Tuber pinelliae* being filtered and concentrated to form a condensate of *Tuber pinelliae*; said condensate of *Tuber pinelliae* being granulated by spray-drying;

extracting *Radix glycyrrhizae* in water by decocting; said water extract of *Radix glycyrrhizae* being filtered and concentrated to form a condensate of *Radix glycyrrhizae*; said condensate of *Radix glycyrrhizae* being granulated by spray-drying;

extracting *Radix pancis quinquefolii* in water by decocting; said water extract of *Radix pancis quinquefolii* being filtered and concentrated to form a condensate of *Radix pancis quinquefolii*; said condensate of *Radix pancis quinquefolii* being granulated by spray-drying;

extracting *Herba tridacis procumbentis* in alcohol under refluxing; said *Herba tridacis procumbentis* being filtered and concentrated to form a condensate of *Herba tridacis procumbentis*; said condensate of *Herba tridacis procumbentis* being granulated by spray-drying;

mixing the granules of *Tuber pinelliae, Radix glycyrrhizae, Radix pancis quinquefolii,* and *Herba tridacis procumbentisi* and the condensate of *Tuber ophiopogonis* together to form mixed granules.

18. The method according to claim 17, wherein said alcohol extract of *Herba tridacis procumbentis* is 50% alcohol extract.

19. The method according to claim 17, wherein an excipient is added to each of said condensate of *Tuber pinelliae, Radix glycyrrhizae, Radix pancis quinquefolii,* and *Herba tridacis procumbentisi* to form a herbal paste before granulation.

20. The method according to claim 19, wherein said excipient to be used with said herbal condensate to form the herbal paste is corn starch.

21. The method according to claim 17, wherein said mixed granules are encapsulated.

22. The method according to claim 15, wherein a solid content of said condensate of *Tuber ophipogonis* is about 20–30% by weight of said *Tuber ophipogonis*; a solid content of said condensate of *Tuber pinelliae* is about 15–25% by weight of said *Tuber pinelliae;* a solid content of said condensate of *Radix glycyrrhiza* is about 15–25% by weight of said *Radix glycyrrhiza;* a solid content of said condensate of *Radix pancis quinquefolii* is about 19–29% by weight of said *Radix pancis quinquefolii;* and a solid content of said condensate of *Herba tridacis procumbenti* is about 5–10% by weight of said *Herba tridacis procumbentis*.

23. The method according to claim 15, wherein said granules of *Tuber pinelliae* is about 20–30% by weight of *Tuber pinelliae* raw material; said granules of *Radix glycyrrhizae* about 16–26% of *Radix glycyrrhizae* raw material; said granules of *Radix pancis quinquefolii* is about 27–37% by weight of *Radix pancis quinquefolii* raw material; and said granules of *Herba tridacis procumbentis* is about 37–47% by weight of *Herba tridacis procumbentis* raw material.

24. The method according to claim 17, wherein each of said condensate is condensed by decompressed condensation at a temperature of about 55° C. and a vacuum of about 30 torr.

25. The method according to claim 17, wherein each of said condensate is spray-dried at an inlet temperature of about 105° C. and an outlet temperature of about 76–77° C.

* * * * *